United States Patent [19]

Marzotto

[11] Patent Number: 4,606,290

[45] Date of Patent: Aug. 19, 1986

[54] PROCESS FOR THE MANUFACTURE OF A WOOL FABRIC FOR BEDS, MORE PARTICULARLY A MATTRESS COVER, AND FABRIC OBTAINED BY SAID PROCESS

[75] Inventor: Gaetano Marzotto, Cornedo, Italy

[73] Assignee: Manifattura Lane Gaetano Marzotto & Figli S.p.A., Vicenza, Italy

[21] Appl. No.: 722,730

[22] Filed: Apr. 11, 1985

[30] Foreign Application Priority Data

Apr. 13, 1984 [IT]  Italy ................................. 20535 A/84
May 8, 1984 [IT]  Italy ............................. 21721/84[U]
Sep. 21, 1984 [IT]  Italy ................................. 22760 A/84

[51] Int. Cl.<sup>4</sup> ........................ A47C 31/00; B32B 5/08; B32B 7/08
[52] U.S. Cl. ........................................ 112/429; 5/500; 26/15 R; 112/436; 428/922
[58] Field of Search ..................... 5/499, 500; 112/429, 112/436; 428/922; 26/15 R

[56] References Cited

U.S. PATENT DOCUMENTS

| | | | |
|---|---|---|---|
| 668,684 | 2/1901 | Kelly | 112/429 |
| 4,074,107 | 2/1978 | Moss | 5/500 |
| 4,078,107 | 5/1978 | Betterice et al. | 428/922 |
| 4,233,701 | 11/1980 | Barnard et al. | 5/499 |
| 4,307,144 | 12/1981 | Sanders et al. | 428/922 |

Primary Examiner—James C. Cannon
Attorney, Agent, or Firm—Laff, Whitesel, Conte & Saret

[57] ABSTRACT

The process for the manufacture of a wool fabric to be used as a mattress cover comprises four steps in succession, that is a loosening step, a shearing step, a moistening step and a pressing step, and further trimming steps for applying elements of electrically conductive material to said fabric as well as at least a shunt for grounding the same elements.

The wool fabric 16 thus obtained comprises wool yarns having a substantially reduced length and sticking fast to the weft of the fabric itself, as well as elements 104, 106 of electrically conductive material and at least a shunt 108 for grounding the elements 104, 106 and adapted to allow the electrostatic energy to be discharged from a sleeping person.

14 Claims, 4 Drawing Figures

PROCESS FOR THE MANUFACTURE OF A WOOL FABRIC FOR BEDS, MORE PARTICULARLY A MATTRESS COVER, AND FABRIC OBTAINED BY SAID PROCESS

FIELD AND BACKGROUND OF THE INVENTION

The present invention relates to a process for the manufacture of a wool fabric for beds, more particularly a mattress cover, and to the fabric obtained by said process.

It is known that wool fabrics and blankets are susceptible of being easily worn out and do not stand strong pressures and/or rubbings. In fact wool flocks and yarns inevitably tend to twist and clot in an uneven manner when they are submitted to strong stresses. As a result, when the yarns are so entangled and tensioned the wool loses most of its physical characteristics. For those reasons wool blankets have always been disposed over a sleeping person and never viceversa as they cannot endure the weight of a person and the movements she or he makes without getting spoilt due to the occurrence of the above mentioned phenomena also called "pilling".

Studies carried out by the same applicant have however proved that thermal insulation is necessary and important not only over a resting person by means of the traditional blankets, but also under the same, close to the mattress. In fact it has been found that about 40% of heat disperses in the mattress direction and that therefore a good protection given by blankets might be insufficient or cause lack of equilibrium between the different parts of a body alternatively turned towards the blankets and the mattress.

On the other hand it is known that a thermal insulation in the region of the mattresses is very difficult when it is not accomplished by the mattresses themselves. In fact as an additional insulating material it is not possible to use either wool blankets or other perspiration-reducing fabrics or fibers. This is due to the fact that the direct pressure exerted by a person lying on those fabrics immediately causes an excessive humidification of the same. As a consequence of that only cotton covers are laid over mattresses these covers only aiming at preventing the mattress from being soiled or spoilt and not at increasing its thermal insulation.

Further studies carried out by the same applicant have also proved that for a person lying on a bed not only a correct heat distribution and a good perspiration are important but also the dispersion of the electrostatic energy previously stored. In fact the experience teaches that the normal movements of a person give rise to a great storage of electrostatic charges. For example, said electrostatic charges are produced in working areas or buildings where floors are covered with moquette and they do not disperse upon contact with a bed. In fact the portion of bed contacting a resting person is substantially insulated from the ground and moreover the spontaneous movements of a resting person can remarkably increase the electrostatic energy on a human body.

Some experiments carried out by the same applicant have proved that even people who during their normal daylife live in environments that do not promote the storage of electrostatic charges, may store an electrostatic energy of substantially at least 30 nanocoulombs while sleeping, due to the above mentioned rubbing movements against a bed.

Under that situation it appears evident that it is important to eliminate the electrostatic energy too in order to achieve an optimum physiological rest. However eliminating this electrostatic energy appears difficult: none of the different elements of which bed fabrics consist is electrically conductive. More particularly covers disposed on mattresses and directly in contact with a resting person are not conductive.

OBJECTS

The technological task of the present invention is therefore to accomplish a process for manufacturing a wool fabric for beds adapted to obviate the above mentioned drawbacks.

Within the scope of this general task it is an important object of the present invention to make available a wool fabric for beds, particularly a mattress cover, which while maintaining all positive characteristics proper to wool may be able to stand rubbing stresses and wear and also to eliminate all electrostatic charges.

SUMMARY OF THE INVENTION

The foregoing object is substantially attained by a process for manufacturing a wool fabric for bed, in particular a mattress cover comprising four steps in succession, that is a loosening step, a shearing step, a moistening step and a pressing step, and further trimming steps for applying elements of electrically conductive material to said fabric as well as at least a shunt for grounding the same elements.

The wool fabric obtained by way of the above process is characterized in that it exhibits wool yarns of substantially reduced length sticking fast to the fabric weft in a uniform manner as well as elements made of electrically conductive material and at least a shunt for grounding said elements and adapted to allow the electrostatic energy to be discharged.

BRIEF DESCRIPTION OF THE DRAWINGS

Further features will become more apparent from the description of a preferred embodiment given by way of example only with reference to the accompanying drawings in which.

DESCRIPTION OF THE PREFERRED EMBODIMENT

Figures 1, 2:
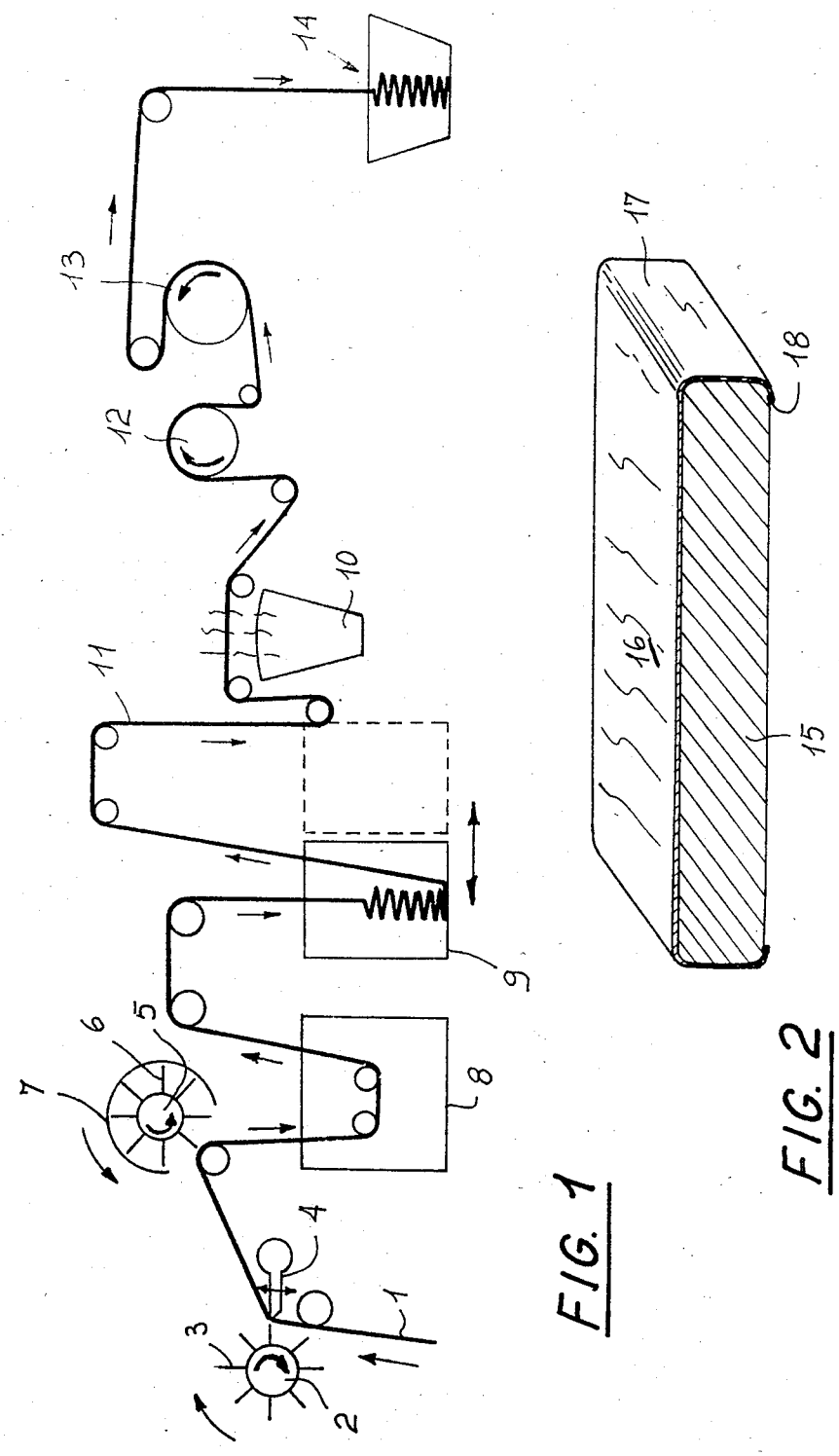
FIG. 1 diagrammatically shows some processing steps of the wool fabric of the invention.
FIG. 2 diagrammatically shows a mattress over which a mattress cover obtained by means of the above processes has been spread.

Referring to the figures, the process is defined by a number of steps allowing to obtain a finished product starting from a raw wool fabric 1 not yet processed as to its physical characteristics and to the structure of its flocks or hair.

First the raw fabric 1 undergoes a loosening step. During this step the fabric is caused to pass in contact with a working roller 2 which, by means of projections 3, pulls out the wool flocks and gives them a uniform direction. The action of the working roller 2 is more or less strong depending upon its working depth on the raw material 1 and that depth can be adjusted by an oscillating support 4 disposed under the fabric so that it backs it up.

After the loosening step the fabric is submitted to a shearing step, during which it moves along and contacts a shearing roller 5 provided with a number of substantially radial blades 6 that clip the previously raised wool flocks. The shearing roller 5 is surrounded by a cover 7 connected to suction means so that the cut wool can be removed.

Advantageously just after the shearing step an additional suction step takes place during which all the hair that is not fixedly fastened to the fabric is removed. This additional suction step is performed while the fabric is being passed inside a suction unit 8.

Then an intermediate storage step is provided during which the fabric is lapped and piled up in appropriate carriages 9. Said carriages 9 are sent to a further station where the processing goes on.

The third step consists in moistening the semi-finished fabric, now identified at 11, by means of a vaporization device 10. Then a fourth pressing step follows during which the semifinished fabric 11 is heated and pressed so that the wool flocks may uniformly stick fast to the fabric weft. For carrying out this operation the fabric is tensioned and caused to slide along at least a pair of heating rollers 12 and 13. When the fabric 11 is brought into contact with the first roller 12, provided with a rotary movement and heated by the steam passing inside it, one surface thereof is pressed, the other surface of the fabric 11 being pressed when the fabric itself is brought into contact with the second roller 13 which is also rotating and heated by inner steam. In the figure, by way of example only, some idler pulleys are shown which ensure the correct sliding of the fabric 11 and therefore a processing on both faces of the same, but is obvious that the number of such idler pulleys may be whatever as well as that of said heating rollers.

After the pressing step the fabric is sent to suitable storage devices and afterwards to further working stations to be described later.

Anyway a fabric as obtained after the above steps is already a wool fabric in which the wool yarns are uniformly adherent to the fabric weft. The uniform disposition of the wool yarns is ensured by the processes carried out during the first and second steps, that is loosening and shearing, while the adhesion of said yarns is ensured by the third and fourth steps, that is moistening and pressing. Practically the fabric thus obtained has the same thermal insulation as the traditional wool blankets but it looks much thinner and above all insensitive to rubbings and wearings and not subjected to pilling. This fabric can already be used as a mattress cover.

FIG. 2 shows this particular use and represents a mattress 15 of any kind over which a suitably sized wool fabric identified at 16 has been spread, said fabric exactly covering the upper surface of mattress 15. In addition the edges of the wool fabric 16 are associated with flaps 17 made of a different material, possibly provided at their corners with an elastic lace 18 designed for allowing a good and steady wrapping of the mattress.

However the process according to the invention also provides further working steps consisting in additionally applying elements made of electrically conductive material thereto and at least a shunt for grounding said elements.

These final working steps which may be preceded by other particular treatments, such as mothproof and shrink-proof treatments, are accomplished by applying tapes 105 provided with wires 104 to the wool fabric 16.

Advantageously during the manufacture of said tapes 105 one or more copper wires 104 are already interlaced therewith; more particularly the copper wires 104 are arranged so that, together with other threads for example of cotton, they may form the warp yarns and be fixed to the weft yarns. Tapes 105 are applied transversely to the fabric and they terminate close to the fabric borders.

Around said borders, that is following the contour of the wool fabric 16, a further wire 106 is disposed and engaged during a subsequent step. The process for engaging said wire with the fabric is as follows: the wire 106 is arranged close to the fabric borders and is attached thereto by whipstitching. Said whipstitching is the same that is used for trimming the borders of the wool fabric 16. In more detail, the employment of a common sewing machine for industrial use and suitable for whipstitching is provided, the presser foot of which has however to be modified. In fact an opening must be made at the front of said foot; the wire 106 fed from a suitable reel is introduced into that opening parallelly to the borders and is clamped between the foot and the feed dog and pulled along by the latter together with the wool fabric 16 while the whipstitching is executed thereon. The function of said stitching is also to allow the enclosing wire 106 and the copper wires 104 incorporated with tapes 105 to become electrically integral to each other. In fact said stitching is carried out on the ends of tapes 105 too.

During subsequent steps it is also possible to fasten elastic laces to the fabric corners as well as a shunt that from said enclosing wire leads to a grounding whatever. According to the invention however said further working steps are carried out at the same time and together with the stiching along the wool fabric borders and the engagement of the enclosing wire 106 therewith. In fact said elastic laces identified at 103 as well as the shunt 108 are fastened to the border of the wool fabric 16. So the elastic laces 103 at least partially overlap the end portions of tapes 105 and are fastened thereto while the shunt 108 extends from one of said end portions.

Figure 4:
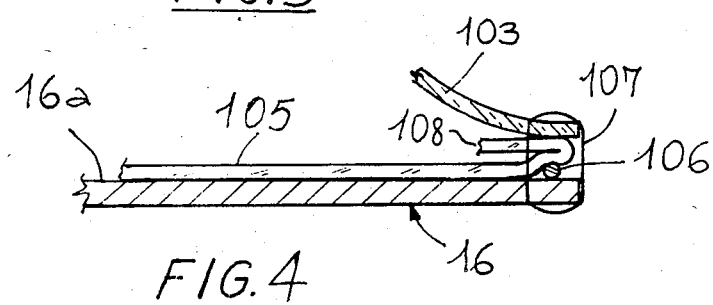
FIG. 4 is a section view of the mattress cover seen in FIG. 3 taken along line IV—IV of said FIG. 3.

The engagement of all the above mentioned elements is achieved by disposing the same in a folded down position as seen in FIG. 4, so that they do not interfere either with the passage of the sewing machine or with that of shears normally associated with the sewing machine and used for trimming the fabric.

Figure 3:
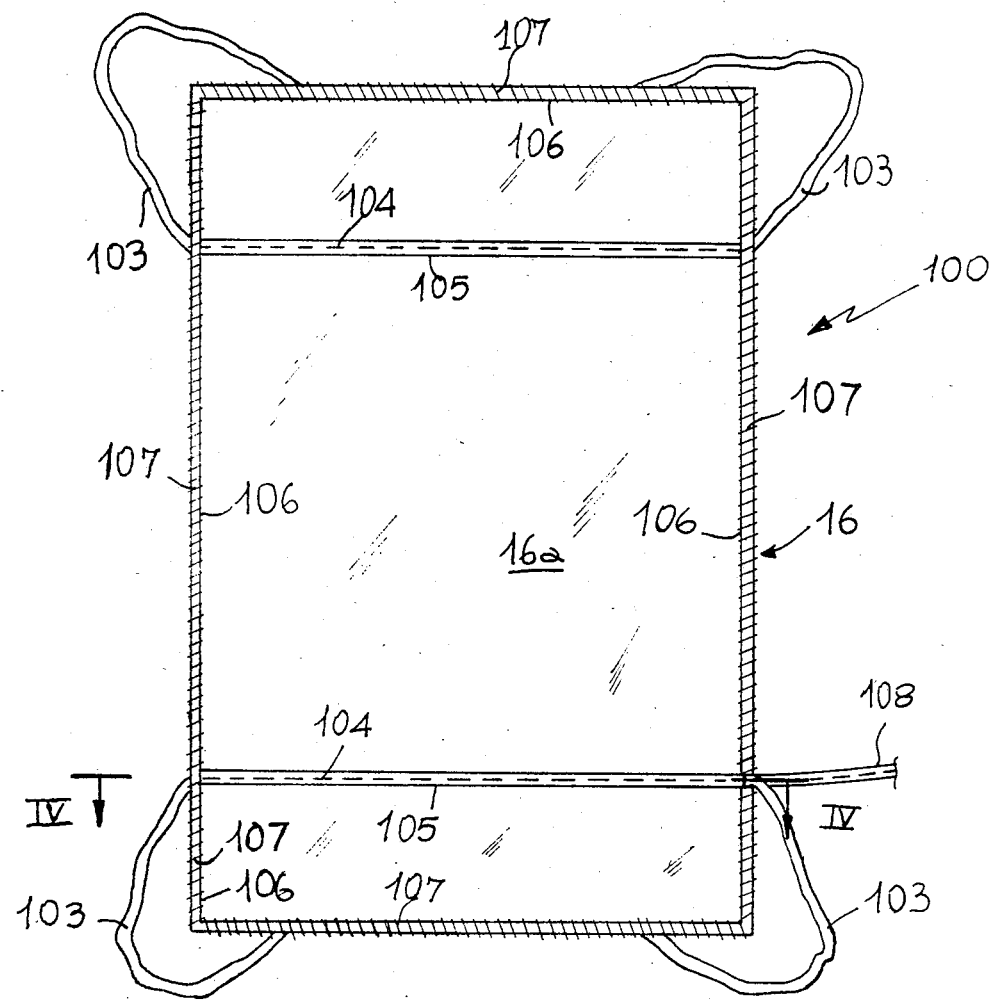
FIG. 3 is a detailed view of a finished mattress cover.

The mattress cover accomplished by the process of the invention is globally indicated at 100 in FIG. 3. It comprises the wool fabric 16, made to the measure of the underlying mattress and fixed to the latter by the elastic laces 103 arranged at the corners of the wool fabric 16. Furthermore, elements of electrically conductive material consisting of wires, preferably copper wires, are arranged on said wool fabric in an original manner. In more detail, two copper wires 104 cross the wool fabric 16 and are disposed parallelly to each other. Wires 104 are integral to tapes 105 applied to the upward face 16a of the wool fabric 16 and are therefore in contact with the body of a sleeping person. Tapes 105 are engaged with the face 16a in any suitable manner.

Besides the two transverse wires 104 a further wire 106, preferably made of copper too, substantially surrounds the wool fabric 16 and is disposed on the face 16a of the same, close to the borders thereof. The enclosing wire 106 is engaged by means of a whipstitching 107 which is the same used for trimming the borders of the wool fabric 16. The enclosing wire 106 is in contact with the ends of the transverse wires 104.

A shunt 108 adapted to establish a grounding extends from the enclosing wire 106; it consists of wires too, preferably copper wires, incorporated with a tape.

Advantageously the tapes 105 connected to the transverse wires 104 lead off to the regions to which the elastic laces 103 are attached; it is also from one of said regions that the shunt 108 extends. FIG. 4 is a sectional view of one of said connection areas and particularly the one from which also the shunt 108 projects. As it is possible to see from said figure a further original configuration of the mattress cover 100 consists in that the shunt 108 is but an extension of one of the transverse wires 104 together with its respective tape 105. In addition the whipstitching 107 along the wool fabric borders also simultaneously engages each tape 105, each elastic lace 103, the shunt 108 and the enclosing wire 106.

The mattress cover thus achieved has proved to be very advantageous. Experimental tests carried out by the same applicant have shown that said mattress cover can ensure a body temperature, as to the body part in contact with the mattress, of 37° C., when the outside temperature is 16° C.

Furthermore the dry fabric absorbs 19% of dampness by weight, which corresponds to 62.7 g of water per square meter. Thus it eliminates 70-80% of the body humidity and protects from outside dampness. It also allows a considerable perspiration: it permits the passage of more than 200 l of air per minute, every 20 cm$^2$. Thus human toxins are eliminated and an excellent welfare condition is created.

In addition said mattress cover is fire-proof and shrink-proof.

Besides it is to be noted that this invention makes available a fabric capable of immediately ground discharging all the electrostatic energy carried by a sleeping person or formed as a consequence of the movements executed by that person while sleeping. In fact experimental tests have proved that also when relatively high electrostatic charges are concerned, for example on the order of 40 nanocoulombs, the contact with said fabric leads to an immediate ground discharge of the electrostatic charges. In a bed provided with said fabric the residual electrostatic charges become stable on a substantially negligible residual level, equal to 2-3 nanocoulombs.

It should also be understood that the extremely positive effect of the mattress cover is not reduced if a sheet is disposed on said mattress cover: owing to the thinness of the sheet and to the normal perspiration or humidity produced by a person while sleeping the electrical contact can always be ensured.

Furthermore the introduction of elements of electrically conductive material does not hinder the normal steps for the manufacture of said mattress cover and the various electrically conductive materials are fixedly engaged with the mattress cover by means of easy and quick operations.

The structure thus obtained is particularly strong and moreover the tapes partially aligned with the elastic laces act as a reinforcement to the fabric at the points in which the latter is tensioned by the elastic laces.

What is claimed is:

1. A process of manufacturing a wool fabric capable of withstanding rubbing stresses and wear and eliminating electrostatic charges wherein a raw wool fabric is subjected to a loosening step during which wool flock is pulled out from the fabric and given a uniform direction; the loosened fabric is subjected to a shearing step to clip the previously raised flock; the sheared fabric is subjected to a moistening step and the moistened fabric is subjected to a pressing step to enhance uniform adhesion of flock to the fabric weft; and said pressed fabric is subjected to further trimming steps to apply electrically conductive elements thereto as well as a shunt for grounding said elements.

2. The process according to claim 1 wherein between said shearing and moistening steps is provided an additional suction step, aiming at removing all the wool hair that is not fixedly fastened to the fabric.

3. The process according to claim 1, wherein the moistening step consists in impregnating the wool fabric with steam.

4. The process according to claim 1 wherein the pressing step consists in heating and pressing the wool fabric on both its surfaces by means of heating rollers.

5. The process according to claim 1 wherein said further trimming steps consist in applying electrically conductive wires, preferably copper wires, to the wool fabric both transversely to the same and along its contour, the enclosing wire being brought into electrical contact with the wires disposed transversely and the grounding being defined by a further wire.

6. The process according to claim 5 wherein said transversely disposed wires and said further wire defining the grouding are applied to said wool fabric by means of tapes into which said wires are directly woven as normal warp yarns.

7. The process according to claim 5 wherein said enclosing wire is engaged with the wool fabric by the same whipstitching that is used for trimming the borders of the fabric itself.

8. The process according to claim 7 wherein said whipstitching used for trimming the wool fabric borders is also used for engaging the wool fabric with elastic laces wrapping the mattress corners and with said grounding.

9. The wool fabric produced by the process of claim 1.

10. The wool fabric produced by the process of claim 5.

11. The fabric of claim 10 wherein the further grounding wire consists of an extension of one of the wires applied transversely to the fabric.

12. The wool fabric produced by the process of claim 6.

13. The wool fabric produced by the process of claim 7.

14. The wool fabric produced by the process of claim 8.

* * * * *